United States Patent [19]

Chauvin et al.

[11] Patent Number: 5,496,783
[45] Date of Patent: Mar. 5, 1996

[54] CATALYST FOR THE PRODUCTION OF LIGHT ALPHA OLEFINS BY OLIGOMERIZATION OF ETHYLENE

[75] Inventors: Yves Chauvin, Le Pecq; Dominique Commereuc, Meudon; Francois Hugues, Vernaison; Helene Olivier, Rueil Malmaison; Lucien Saussine, Croissy sur Seine, all of France

[73] Assignee: Institut Francais du Petrole, Rueil Malmaison, France

[21] Appl. No.: 253,017

[22] Filed: Jun. 2, 1994

Related U.S. Application Data

[62] Division of Ser. No. 88,508, Jul. 9, 1993, Pat. No. 5,345,023.

[30] Foreign Application Priority Data

Jul. 9, 1992 [FR] France ................................ 92 08658

[51] Int. Cl.$^6$ .............................. B01J 31/38; C08F 4/642
[52] U.S. Cl. ......................... 502/125; 502/118; 502/126; 502/127; 502/169
[58] Field of Search .................................. 502/118, 125, 502/126, 127, 169

[56] References Cited

U.S. PATENT DOCUMENTS

| | | | |
|---|---|---|---|
| 3,149,097 | 9/1964 | Coover, Jr. et al. | 502/127 |
| 3,149,098 | 9/1964 | Price et al. | 502/125 |
| 3,219,648 | 11/1965 | Hill | 502/126 |
| 3,296,338 | 1/1967 | Jezl et al. | 502/126 |
| 3,882,046 | 5/1975 | Pomogailo et al. | 502/126 |
| 3,997,622 | 12/1976 | Isa et al. | 585/532 |
| 4,006,199 | 2/1977 | Isa et al. | 585/532 |
| 4,647,550 | 3/1987 | Kohora et al. | 502/126 |
| 4,701,505 | 10/1987 | Fujii et al. | 502/126 |
| 4,855,525 | 8/1989 | Young et al. | 585/523 |

FOREIGN PATENT DOCUMENTS

| | | | |
|---|---|---|---|
| 0241596 | 10/1987 | European Pat. Off. | |
| 2669921 | 6/1992 | France. | |
| 2044343 | 4/1971 | Germany. | |
| 44-4555 | 2/1969 | Japan | 502/126 |
| 46-38249 | 11/1971 | Japan | 502/126 |
| 91/02707 | 3/1991 | WIPO. | |

*Primary Examiner*—E. Rollins Cross
*Assistant Examiner*—Walter D. Griffin
*Attorney, Agent, or Firm*—Millen, White, Zelane, & Branigan

[57] ABSTRACT

Process for oligomerizing ethylene into light alpha olefins, mainly 1-butene, 1-hexene, 1-octene and 1-decene, in which the ethylene is contacted with a catalyst obtained by mixing a zirconium compound with an organic compound chosen from within the class of acetals and ketals and with a chlorine or bromine-containing compound of aluminium hydrocarbyl.

12 Claims, No Drawings

CATALYST FOR THE PRODUCTION OF LIGHT ALPHA OLEFINS BY OLIGOMERIZATION OF ETHYLENE

This application is a divisional of application Ser. No. 08/088,508, filed Jul. 9, 1993 now U.S. Pat. No. 5,345,023.

The present invention relates to a process for oligomerizing ethylene to light alpha olefins, mainly 1-butene, 1-hexene, 1-octene and 1-decene.

In U.S. Pat. No. 2,943,125, K. Ziegler describes a method for dimerizing ethylene into 1-butene by means of a catalyst obtained by mixing a trialkyl aluminum and a zirconium or titanium tetraalkoxide.

The oligomerization of ethylene into alpha olefins of varied molecular weights is known and involves either a stoichiometric chain growth reaction, e.g. from an organoaluminic compound, or a catalytic reaction using metals such as titanium, zirconium, chromium, nickel or rare earths, e.g. in Ziegler-type formulations.

Numerous zirconium compounds have been produced for oligomerizing ethylene into alpha olefins, often associated with various complex compounds.

Reference can e.g. be made to the use of zirconium halides combined with esters, ketones, ethers, amines. nitriles, anhydrides, chlorides of acids, amides or aldehydes described in U.S. Pat. No. 4,855,525 and WO 91 02707. or the use of the same zirconium halides combined with ligands selected from among groups of sulphur, phosphorus or nitrogen compounds, described in EP-A-241 596 and EP-A-328 728.

The products obtained with the above catalytic formulations are mainly constituted by alpha olefins having a chain length between $C_{10}$ and $C_{18}$. These mixtures are suitable for uses hitherto allocated to oligomers, plasticizers and detergents.

It is known that most of these catalysts lead to the formation, in addition to the desired alpha olefins, of varying quantities of high molecular weight polymers, which considerably interfere with working.

SUMMARY OF THE INVENTION

The present invention has found that the catalysts obtained by mixing a zirconium compound with at least one organic compound chosen from within the class of acetals of aldehydes and ketals of ketones and with at least one particular aluminum compound, have an unexpected selectivity for the formation of lower oligomers, mainly 1-butene, 1-hexene, 1-octene and 1-decene, which are used as comonomers with ethylene in the production of the linear low density polyethylene or as a starting base for synthetic lubricating oils.

Apart from the improvement of the selectivity for light alpha olefins, the catalysts described in the present invention also aim at reducing the byproduct polymer to a very small amount.

The zirconium compounds used in the invention comply with the general formula $ZrX_xY_yO_z$, in which X is a chlorine or bromine atom and Y is a radical chosen from among RO— alkoxy, $R_2N$-amido or RCOO— carboxylate groups, R being a hydrocarbyl and preferably alkyl radical having 1 to 30 carbon atoms, whilst x and y can assume integral values of 0 to 4 and z is equal to 0 or 0.5, the sum $x+y+2z$ being equal to 4. For example, reference can be made to zirconium halides such as zirconium tetrachloride $ZrCl_4$, zirconium tetrabromide $ZrBr_4$, alkoxides such as zirconium tetrapropylate $Zr(OC_3H_7)_4$, zirconium tetrabutylate $Zr(OC_4H_9)_4$, carboxylates such as zirconium tetraethyl-2-hexanaate $Zr(OCOC_7H_{15})_4$ or oxacarbaxylates such as dizirconium oxo hexaethyl-2-hexanoate $[Zr(OCOC_7H_{15})_3]_2O$.

The organic compounds chosen from among the class of acetals and ketals used in the invention result from the condensation of an aidehyde or a ketone with a monoalcohol or a polyalcohol, e.g. a glycol. They comply with the following general formula:

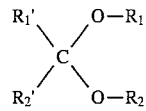

in which $R_{1'}$ and $R_{2'}$ are constituted by a hydrogen atom or a hydrocarbyl radical having 1 to 30 carbon atoms and $R_1$ and $R_2$ are hydrocarbyl radicals having 1 to 30 carbon atoms. The two radicals $R_{1'}$ and $R_{2'}$ and the two radicals $R_1$ and $R_2$ can be the same or different and can also form part of a cycle. The following examples are given: diethoxy methane, diisopropoxy methane, diethoxy-1,1-ethane, diisobutoxy-1,1-ethane, dimethoxy- 1,1-decane, 2-nonyl-1, 3-dioxolan, dimethoxy-2,2-propane, dibutoxy-2,2-propane, dioctoxy-2,2-propane, dimethoxy-2,2-octane dimethoxy-1, 1-cyclohexane and di(ethyl-2-hexyloxy)-2,2-propane.

The aluminum compounds used in the invention are represented by the general formula $AlR''_nX_{3-n}$, in which R'' is a hydrocarbyl radical, preferably alkyl, which has 1 to 6 carbon atoms, X is chlorine or bromine atom and preferably a chlorine atom and n is a number between 1 and 2 and can also in particular be 1, 1.5 or 2.

For example, reference is made to chlorodiethyl aluminum, dichloroethyl aluminum, ethyl aluminum sesquichloride or mixtures thereof.

The catalyst components can be contacted in a random order within a hydrocarbon, e.g. a saturated hydrocarbon such as hexane or haptone and/or an aromatic hydrocarbon such as toluene and/or one or more oligomerization byproducts such as higher oligomers. Preferably, the zirconium compound is firstly mixed with acetal or ketal and then the aluminum compound is added thereto.

The molar ratio between the acetal or ketal and the zirconium compound is approximately 0.1:1 to 5:1 and is preferably approximately 0.5:1 to 2:1. The molar ratio between the aluminum compound and the zirconium compound is approximately 1:1 to 100:1, preferably approximately 5:1 to 50:1 . The zirconium concentration in the thus prepared catalytic solution is advantageously between $10^{-4}$ and 0.5 mole per liter and preferably between $2.10^{-3}$ and 0.1 mole per liter. The temperature at which the three components are mixed is normally between $-10°$ and $+150°$ C., preferably between $0°$ and $+80°$ C. and e.g. equal to ambient temperature ($15°$ to $30°$ C.). Mixing can take place under ethylene or an inert gas atmosphere.

The thus obtained catalytic solution can be used as it is or can be diluted by adding products of the reaction.

In an embodiment of the discontinuous performance of the oligomerization catalytic reaction, a chosen volume of the catalytic solution prepared in the manner described hereinbefore is introduced into a reactor equipped with conventional stirring and cooling systems, followed by pressurization with ethylene to a pressure generally between 0.5 and 15 MPa and preferably between 1 and 10 MPa. The temperature is generally maintained at between $20°$ and $180°$ C., preferably between $40°$ and $150°$ C. The oligomerization reactor is supplied with ethylene at constant pressure until the total liquid volume produced represents between 2 and 50 times the volume of the initially introduced catalytic solution. The catalyst is then destroyed, e.g. by adding water, followed by the removal and separation of the products of the reaction and any solvent.

In the case of continuous operation, the procedure is preferably as follows. The catalytic solution is injected at the same time as the ethylene into a reactor stirred with conventional mechanical means or by an external recirculation. It is also possible to separately inject the components of the catalyst into the reaction medium, e.g. the interaction product of the zirconium compound with the acetal (or ketal) on the one hand and the hydrocarbyl-aluminum halide on the other. The temperature is maintained at between 20° and 180° C., preferably between 40° and 150° C. and the pressure is generally adjusted between 0.5 and 15 MPa. By means of an expansion valve, which keeps the pressure constant, there is an outflow of part of the reaction mixture at a mass flow equal to that of the fluids introduced. The thus expanded fluid is fed into a distillation column system making it possible to separate the oligomers from the ethylene on the one hand, whereby said ethylene can be returned to the reactor, and then the individual oligomers on the other. The heavy products containing the catalyst can be incinerated.

The following examples illustrate the invention without limiting its scope.

EXAMPLE 1

Into a stainless steel autoclave having a useful volume of 250 ml and equipped with a double envelope making it possible to regulate the temperature by circulation of water, is introduced in successive manner and under an argon atmosphere and at ambient temperature: $0.2 \times 10^{-3}$ mole of the complex $[(C_7H_{15}COO)_3Zr]_2O$ in which $C_7H_{15}COO$ is a 2-ethyl hexanoate residue, 50 ml of haptone and then, by means of a hypodermic syringe, 20.8 mg of dimethoxy-2,2-propane (i.e. $0.2 \times 10^{-3}$ mole). After a few minutes introduction takes place of $2.4 \times 10^{-3}$ mole of chlorodiethyl aluminum in solution in 10 ml of heptane.

The temperature is then raised to 75° C., whilst introducing ethylene into the autoclave so as to maintain a constant pressure of 6 MPa. After reacting for 2 hours, ethylene introduction is stopped and the catalyst destroyed by injecting 2 ml of water under pressure. In all, 71 g of ethylene have been consumed.

The composition of the products is given in Table 1. In addition, 0.2% by weight of solid polymer, based on the ethylene consumed, is collected.

EXAMPLE 2 (COMPARATIVE)

Using the same equipment as that in example 1 and under the same conditions, except that the dimethoxy-2,2-propane was omitted, there was a consumption of 96.5 g of ethylene after 15 minutes of reaction. The composition of the products obtained, given in Table 1, shows the beneficial effect of the presence of the ketal in the catalyst on the light alpha olefin selectivity. In addition, collection took place of 8.4% of solid polymer, based on the ethylene consumed, i.e. much more than in example 1.

EXAMPLE 3

Into a 100 ml spherical glass flask placed under an inert atmosphere was transferred so as to be protected from humidity $2 \times 10^{-3}$ mole of sublimated zirconium tetrachloride, followed by the injection by means of a hypodermic syringe of 45 ml of dried, deaerated toluene. The white suspension was stirred at ambient temperature by means of a bar magnet and to the flask was added $2 \times 10^{-3}$ mole of dimethoxy-1,1-decane in solution in 5 ml of toluene, After a few minutes, the zirconium chloride dissolved and the coloring of the thus obtained homogeneous solution evolves from pale yellow, to orange and then to deep red, indicating the formation of a complex.

Into the same autoclave as that described in example 1 successive introduction takes place under an argon atmosphere and at ambient temperature of 5 ml of the complex solution prepared hereinbefore, i.e. $0.2 \times 10^{-3}$ mole of zirconium, 50 ml of heptane and then $1.2 \times 10^{-3}$ mole of ethyl aluminum sesquichloride $Al_2ET_3Cl_3$ in solution in 10 ml of heptane.

The temperature was then raised to 95° C. whilst introducing ethylene into the autoclave, so as to maintain a constant pressure of 6 MPa. Following 2 hours reaction, ethylene introduction was stopped and the catalyst destroyed by the injection under pressure of 2 ml of water. In all, 51 g of ethylene were consumed.

The composition of the products is given in Table 1. Only traces of solid polymer were collected and namely in quantities too small to be accurately measured.

EXAMPLE 4

Using the same equipment and the same operating procedure as described in example 1, except that the dimethoxy-1,1-decane was replaced by diisopropoxy methane in the same proportions, the oligomerization reaction consumed 98.3 g of ethylene in 1 hour.

The composition of the products is given in Table 1. Only traces of solid polymer were collected.

EXAMPLE 5

Using the same equipment and the same operating procedure as described in example 3, except that the dimethoxy-1,1-decane was replaced by dimethoxy-2,2-propane in the same proportions, the oligomerization reaction consumed 77.3 g of ethylene in 1 hour.

The composition of the products is given in Table 1 . Only traces of solid polymer were collected.

EXAMPLE 6

Using the same equipment and with the same operating procedure as described in example 3, except that dimethoxy-1,1-decane was replaced by dioctoxy-2,2-propane in the same proportions, the oligomerization reaction consumed 88.5 g of ethylene in 1 hour.

The composition of the products is given in Table 1. Only traces of solid polymer were collected.

EXAMPLE 7

In the same equipment and with the same operating procedure as described in example 3, except that the dimethoxy-1,1-decane was replaced by a double molar quantity of dimethoxy-2,2-octane (i.e. $0.4 \times 10^{-3}$ mole of ketal for $0.2 \times 10^{-3}$ mole of zirconium used), the oligomerization reaction consumed 39.3 g of ethylene in 3 hours.

The composition of the products is given in Table 1. Only traces of solid polymer were collected.

EXAMPLE 8

Using the same equipment and the same operating procedure as described in example 1, except that the dimethoxy-1,1-decane was replaced by dibutoxy-2,2-propane in the same proportions and that the oligomerization reaction temperature was fixed at 65° C. instead of 95° C., said reaction consumed 44 g of ethylene in 2 hours.

The composition of the products is given in Table 1. Only traces of solid polymer were collected.

EXAMPLE 9

Using the same equipment and with the same operating procedure as described in example 3, except that the dimethoxy-2,2-decane was replaced by dioctoxy- 2,2-propane in the same proportions and that introduction took place of $2.4 \times 10^{-3}$ mole of chlorodiethyl-aluminum in place of $1.2 \times 10^{-3}$ mole of ethyl aluminum sesquichloride, the oligomerization reaction consumed 83.4 g of ethylene in 30 minutes.

The composition of the products is given in Table 1. Collection also took place of 0.47% by weight of solid polymer, based on the ethylene consumed.

EXAMPLE 10

Using the same equipment and the same operating procedure as described in example 9, except that a double quantity of dioctoxy-2,2-propane was used (i.e. $0.4 \times 10^{-3}$ mole of ketal for $0.2 \times 10^{-3}$ mole of zirconium), the oligomerization reaction consumed 58.9 g of ethylene in 2 hours.

The composition of the products is given in Table 1. Collection also took place of 1.35% by weight of solid polymer, based on the ethylene consumed.

EXAMPLE 11

Using the same equipment and the same operating procedure as described in example 3, except that the dimethoxy-2,2-decane was replaced by diisopropoxy methane in the same proportions and that $2.4 \times 10^{-3}$ mole of chlorodiethyl aluminum was introduced in place of $1.2 \times 10^{-3}$ mole of ethyl aluminum sesquichloride and that the oligomerization reaction was performed at 70° C. instead of 95° C., said reaction consumed 69 g of ethylene in 1 hour.

The composition of the products is given in Table 1. Collection also took place of 0.86% by weight of solid polymer, based on the ethylene consumed.

EXAMPLE 12 (COMPARATIVE)

Using the same equipment and the same operating procedure as described in example 3, except that di-methoxy-1,1-decane was not introduced (so that the zirconium tetrachloride was introduced in suspended state into the autoclave), the reaction consumed 32.8 g of ethylene in 4 hours.

The composition of the products given in Table 1 shows a poor selectivity for light alpha olefins. A large amount of polymer, equal to 15% by weight, based on the ethylene consumed, was collected.

This example illustrates the double improvement resulting from the introduction of an acetal with respect to the selectivity for light alpha olefins and the reduction of the byproduct polymer level.

TABLE 1

| EXAMPLE | DISTRIBUTION OF PRODUCTS OBTAINED (wt. %*) | | | | | ALPHA OLEFIN CONTENT (wt. %) | |
|---|---|---|---|---|---|---|---|
| | $C_4$ | $C_6$ | $C_8$ | $C_{10}$ | $C_{12^+}$ | in $C_4$ | in $C_6$ |
| 1 | 44.1 | 31.2 | 14.1 | 6.1 | 4.4 | >99 | 94.9 |
| 2 | 30.6 | 24.1 | 15.6 | 10.0 | 11.3 | 99.6 | 88.5 |
| 3 | 22.3 | 24.6 | 18.2 | 12.2 | 23.2 | 98.9 | 97.8 |
| 4 | 17.0 | 20.8 | 18.0 | 13.7 | 31.1 | 99.5 | 98.0 |
| 5 | 20.9 | 23.9 | 19.0 | 13.3 | 23.2 | 99.0 | 96.6 |
| 6 | 18.4 | 21.1 | 17.8 | 14.0 | 29.2 | 99.6 | 96 |
| 7 | 39.1 | 29.3 | 15.1 | 7.6 | 9.9 | 97.6 | 93.7 |
| 8 | 25.7 | 23.6 | 17.1 | 12.0 | 22.2 | 99.0 | 96.7 |
| 9 | 28.9 | 28.1 | 18.8 | 10.4 | 13.7 | 99.8 | 96.3 |
| 10 | 33.5 | 28.4 | 16.9 | 9.0 | 11.3 | 99.8 | 98.0 |
| 11 | 42.7 | 31.6 | 14.7 | 6.3 | 4.6 | 99.6 | 98.5 |
| 12 | 11.0 | 12.0 | 11.5 | 9.5 | 41.0 | >99 | 98.0 |

*The compliment to 100 corresponds to the polymer form.

We claim:

1. A catalyst for the conversion of ethylene into light alpha olefins, which comprises:

a zirconium compound of the formula $ZrX_xY_yO_z$, in which X is a chlorine or bromine atom, Y is a radical selected from the group consisting of RO—, $(R)_2N$— and RCOO— groups, in which R is a hydrocarbyl radical having 1 to 30 carbon atoms, x and y are 0 or an integer of 1 to 4, and z is 0 or 0.5, the sum x+y+2z being equal to 4, an organic acetal or ketal compound of formula

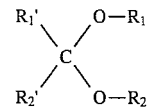

in which $R'_1$ and $R'_2$ are independently a hydrogen atom or a hydrocarbyl radical having 1 to 30 carbon atoms and $R_1$ and $R_2$ are independently hydrocarbyl radicals having 1 to 30 carbon atoms, and an aluminum compound of the formula $AlR''_nX_{3-n}$ in which R" is a hydrocarbyl radical having 1 to 6 carbon atoms, X is a chlorine or bromine atom and n is a number of from 1 to 2, such that the molar ratio of the acetal or ketal compound to the zirconium compound is approximately 0.1:1 to 5:1 and the molar ratio of the aluminum compound to the zirconium compound is approximately 1:1 to 100:1.

2. The catalyst of claim 1, obtained by mixing the zirconium compound and the organic acetal or ketal compound together and then mixing the product thereof with the aluminum compound.

3. The catalyst of claim 1, wherein the organic acetal or ketal compound is selected from the group consisting of diethoxy methane, diisopropoxymethane, 1,1-diethoxyethane, 1,1-diisobutoxy ethane, 1,1-dimethoxy decane, 2-nonyl-1,3-dioxolan, 2,2-dimethoxy propane, 2,2-dibutoxy propane, 2,2-dioctoxy propane, 2,2-dimethoxy octane, 1,1-dimethoxy cyclohexane, and di-(ethyl-2-hexyloxy)-2,2-propane.

4. The catalyst of claim 1, wherein the zirconium compound is selected from the group consisting of zirconium tetrabromide, zirconium tetrapropylate, zirconium tetrabutylate, zirconium-2-tetraethyl hexanoate and dizirconium-2-oxohexaethyl hexanoate.

5. The catalyst of claim 1, wherein the zirconium compound is zirconium tetrachloride.

6. The catalyst of claim 1, wherein the aluminum compound is selected from group consisting of chlorodiethyl aluminum, ethyl aluminum sesquichloride and mixtures thereof.

7. The catalyst of claim 1, wherein the molar ratio between the organic acetal or ketal compound and the zirconium compound is approximately 0.5:1 to 2:1.

8. The catalyst of claim 1, wherein the molar ratio of the aluminum compound to the zirconium compound is approximately 5:1 to 50:1.

9. The catalyst of claim 1, obtained by mixing the zirconium compound, the organic acetal or ketal compound and the aluminum compound together at a temperature of 0° to 80° C. and under an ethylene or inert gas atmosphere.

10. The catalyst of claim 1, wherein R is alkyl of 1–30 carbon atoms and R" is an alkyl radical of 1–6 carbon atoms.

11. The catalyst of claim 1, wherein n is 1, 1.5 or 2.

12. The catalyst of claim 1, wherein y is an integer of 1 to 4.

* * * * *